US006194563B1

(12) United States Patent
Cruickshank

(10) Patent No.: US 6,194,563 B1
(45) Date of Patent: Feb. 27, 2001

(54) SOLID PHASE NUCLEIC ACID LABELING BY TRANSAMINATION

(75) Inventor: Kenneth A. Cruickshank, Naperville, IL (US)

(73) Assignee: Vysis, Inc., Downers Grove, IL (US)

( * ) Notice: Subject to any disclaimer, the term of this patent is extended or adjusted under 35 U.S.C. 154(b) by 0 days.

(21) Appl. No.: 09/277,087

(22) Filed: Mar. 26, 1999

(51) Int. Cl.$^7$ .............. C12Q 1/68; C07H 19/00; C07H 21/00; C07H 21/02; C07H 21/04
(52) U.S. Cl. .............. 536/25.3; 435/6; 536/22.1; 536/23.1; 536/25.3; 536/25.4
(58) Field of Search .............. 435/6; 536/22.1, 536/23.1, 25.3, 25.4, 25.32

(56) References Cited

U.S. PATENT DOCUMENTS

| 5,082,935 | 1/1992 | Cruickshank | 536/27 |
| 5,215,882 | * 6/1993 | Bahl et al. | 435/6 |
| 5,491,224 | 2/1996 | Bittner et al. | 536/22.1 |
| 5,506,350 | 4/1996 | Bittner et al. | 536/55.3 |
| 5,736,626 | 4/1998 | Mullah et al. | 536/25.3 |

OTHER PUBLICATIONS

Cruickshank et al., "Simultaneous Multiple Analyte Detection Using Fluorescent Peptides and Capillary Isoelectric Focusing", Journal of Chromatography A 817:41–47, 1998.
Draper, "Attachment of Reporter Groups to Specific, Selected Cytidine Residues in RNA Using a Bisulfite–catalyzed Transamination Reaction", Nucleic Acids Research 12:989–1002, 1984.
Gillam et al., "N$^4$–(6–Aminohexyl)cytidine and –deoxycytidine Nucleotides Can Be Used to Label DNA", Analytical Biochemistry 157:199–207, 1986.
Hayatsu, "Bisulfite Modification of Nucleic Acids and Their Constituents", Prog. Nulceic Acid Res. Molec. Biol. 16:75–124, 1976.
Reisfeld et al., "Nonradioactive Hybridization Probes Prepared by the Reaction of Biotin Hydrazide with DNA", Biochemical and Biophysical Research Communications 142:519–526, 1987.
Schulman et al., "Attachment of Protein Affinity–labeling Reageants of Variable Length and Amino Acid Specificity to E. coli tRNA$^{fMet}$", Nucleic Acids Research 9:1203–1217, 1981.
Sono et al., "Role of Bisulfite in the Deamination and the Hydrogen Isotope Exchange of Cytidylic Acid", Journal of the American Chemical Society 95:4745–4749, 1973.
Summerton, "Sequence–Specific Crosslinking Agents for Nucleic Acids: Design and Functional Group Testing", J. Theor. Biol. 78:61–75, 1979.

* cited by examiner

*Primary Examiner*—Jezia Riley
(74) *Attorney, Agent, or Firm*—Norval B. Galloway

(57) ABSTRACT

The invention relates to a method for linking a detectable label to a nucleic acid by (1) providing a nucleic acid bound to a solid support, the nucleic acid having a cytidine base; (2) transaminating the cytidine base with a reactive group to form a covalent linkage between the cytidine base and the reactive group; and (3) linking a detectable label to the reactive group. The invention also includes compositions containing a labeled nucleic acid produced by the methods of the invention immobilized on a solid support, and a kit containing a solid support, a bisulfite, a reactive group, and a detectable label.

27 Claims, No Drawings

SOLID PHASE NUCLEIC ACID LABELING BY TRANSAMINATION

FIELD OF THE INVENTION

The invention relates to nucleic acid labeling chemistry.

BACKGROUND OF THE INVENTION

The labeling of nucleic acids with detectable probes has been a common molecular biology laboratory technique for decades. In recent years, the development and commercial success of nucleic acid microarrays (sometimes also called biochips) has often relied, in part, on the use of labeled nucleic acid probes.

Many nucleic acid labeling techniques require indirect labeling; in other words, the nucleic acids are labeled with one member of a specific binding pair (e.g., biotin), hybridized to a target nucleic acid, and visualized with the other member of the specific binding pair which is detectably labeled (e.g., horseradish peroxidase-labeled streptavidin). Direct labeling of nucleic acids has recently been achieved using bisulfite-catalyzed transamination (BCT) of cytidines within a nucleic acid (U.S. Pat. Nos. 5,506,350 and 5,491,224). However, these direct labeling procedures, performed in solution, are limited by the time (two or more days) required to achieve sufficient labeling of the nucleic acids.

Oligonucleotides are commonly made today using a solid phase methodology in which the oligos are prepared by successive iterative additions of nucleoside monomers while the growing oligonucleotide chain is attached to a solid phase. Oligonucleotides have been modified with single or multiple fluorescent dye molecules while still attached to the synthesis solid phase, e.g., as described in Haralambidis et al., *Nuc. Acids Res.*, 18:501–505, 1990. However, this methodology cannot be applied to complex genomic DNAs such as that extracted from solid tumor samples or blood samples.

SUMMARY OF THE INVENTION

The invention is based on the discovery that nucleic acids immobilized on a solid support can be efficiently and rapidly functionalized with reactive groups by a transamination reaction (e.g., a bisulfite-catalyzed transamination [BCT] reaction). Subsequent to the transamination, the functional groups (typically primary amino groups) can be derivatized with a fluorescent dye and released from the solid phase using a variety of chemical reactions. In general, these reactions should have one or more of the following characteristics: (1) not compromise the fluorescence of the dye, (2) not damage the hybridization properties of the DNA probe, and (3) give high yields of fluorescently labeled nucleic acid product.

A prominent aspect of the invention is the reversibility of the attachment chemistry. For example, efficient attachment of nucleic acids can be achieved using phosphoramidate linkages that are stable to the BCT and dye attachment chemistries, yet permit efficient release of the nucleic acid from the solid support under conditions of elevated pH for DNA stability. Since RNA can be hydrolyzed under elevated pH conditions, the releasing step in labeling RNA may require an alternative release chemistry such as thermal formamide treatment.

Accordingly, the invention features a method for linking a detectable label to a nucleic acid by (1) providing a nucleic acid bound (e.g., covalently bound) to a solid support (e.g., a bead or a chromium-plated glass slide), the nucleic acid including a cytidine base; (2) transaminating (e.g., by a bisulfite-catalyzed reaction) the cytidine base with a reactive group to form a covalent linkage between the cytidine base and the reactive group; and (3) linking a detectable label to the reactive group.

The reactive group can be of the formula:

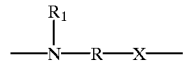

where R is an alkylene radical containing 2 to 14 carbon atoms inclusive, X is

$R_1$ and $R_2$ are each independently selected from the group consisting of hydrogen and a lower alkyl. Further, the reactive group can be $H_2N(CH_2CH_2X)_nCH_2CH_2NH_2$, where n=1–4, X is O, SO, $SO_2$, Si, or $NR_3$, where $R_3$ is a lower alkyl. An example of a reactive group is ethylenediamine.

In the method, the reactive group can be dissolved in a solvent which includes a trihaloacetate chaotrope anion (e.g., trifluoroacetate), the detectable label can be a fluorescent molecule, and the nucleic acid can be about 1 to 2 kilobases in length.

The method optionally includes releasing the nucleic acid from the solid support.

The nucleic acid can be bound to the solid support by reacting a terminal phosphate of a nucleic acid and an amino activated solid support with 1-ethyl-3-(dimethylaminopropyl)carbodiimide.

In another aspect, the invention includes a composition having (1) a solid support; (2) a nucleic acid bound to the solid support, the nucleic acid including a cytidine base; (3) a reactive group covalently linked to the cytidine base; and (4) a detectable label linked to the reactive group (e.g., a bead or a chromium-plated glass slide).

The reactive group includes the formula:

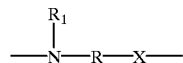

where R is an alkylene radical containing 2 to 14 carbon atoms inclusive, X is

$R_1$ and $R_2$ are each independently selected from the group consisting of hydrogen and a lower alkyl. Further, the reactive group can be $H_2N(CH_2CH_2X)_nCH_2CH_2NH_2$, where n=1–4, X is O, SO, $SO_2$, Si, or $NR_3$, where $R_3$ is a lower alkyl. An example of a reactive group is ethylenediamine.

In addition, the detectable label can be a fluorescent molecule, the nucleic acid can be about 1 to 2 kilobases in length, and the nucleic acid can be covalently bound to the solid support. The nucleic acid can be bound to the solid support by reacting a terminal phosphate of a nucleic acid and an amino activated solid support with 1-ethyl-3-(dimethylaminopropyl)carbo-diimide.

In another aspect, the invention includes a method for linking a detectable label to a plurality of nucleic acids, each of the plurality having a unique sequence, by (1) providing the plurality of nucleic acids bound to a solid support, each of the plurality including a cytidine base; (2) transaminating each cytidine base with reactive groups to form a covalent linkage between each cytidine base and a reactive group; and (3) linking a detectable label to the reactive groups.

In yet another aspect, the invention includes a kit containing (1) a solid support (e.g., a bead), (2) a bisulfite, (3) a reactive group; and (4) a detectable label.

The solid phase BCT labeling procedure described herein can be performed in a matter of hours, a time frame unexpectedly shorter than that required for solution BCT labeling. The new labeling techniques are especially useful for automated or robotic labeling of large numbers of DNA samples. In addition, the performance of solid phase BCT labeling of DNA can be facilitated by kits that include a solid support, a detectable label, and BCT reagents required for labeling.

The development of biochips has reduced the time required for global analysis of a DNA sample by enabling simultaneous measurement of the expression of thousands of genes. However, the total analysis time is, in many cases, limited by the time required to directly label the sample DNA. Thus, by enabling highly efficient and rapid direct labeling of nucleic acids, the methods and kits of the invention further decrease the time required for global DNA analysis.

In addition, the compositions of the invention provide a novel means to analyze a DNA sample. For example, a fluorescently labeled DNA sample immobilized on a solid support can be hybridized to probe DNA containing a different fluorescent label. The presence of a sequence which hybridizes to the probe is then detected by a change in fluorescence color.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention relates to methods of labeling immobilized nucleic acids by transamination reactions, e.g., bisulfite-catalyzed transamination reactions, compositions including BCT-labeled nucleic acids bound to a solid support, and kits sufficient for performing the labeling reactions.

General Methodology

In general, the new method includes at least three steps. In the first step, the nucleic acids to be labeled are isolated and bound to a solid support. In the second step, the cytosines within the immobilized nucleic acid are bound to a reactive group via transamination reaction, e.g., a BCT reaction. Other nucleic acid transamination labeling techniques include bromination/amination (Keller et al., *Anal. Biochem.* 170:441–450, 1998) and chemistries involving platinum-coordinated compounds (European Patent 0539466 B1). In the third step, a detectable label is bound to the reactive group, thereby linking the detectable label to the nucleic acid.

The second and third step can be performed at any time after immobilization of the nucleic acid. For example, the second and third step can be performed concurrently in a single BCT/labeling reaction containing the immobilized nucleic acid, a bisulfite catalyst, and a fluorophore conjugate containing a reactive group. The reactive group can also be attached to the fluorophore before the resulting conjugate is attached to the immobilized DNA.

Linking Nucleic Acids to Solid Supports

Nucleic acids are generally purified or isolated from a biological sample (e.g., a blood sample) to render them suitable for labeling. For example, peripheral blood mono-nuclear cells are isolated from a blood sample. The mRNA is then isolated from those cells, and cDNA synthesized from the mRNA. The cDNA can then be purified by ethanol precipitation or other standard methods before attachment to a solid support. Alternatively, genomic DNA can be isolated from the cells and optionally sheared by sonication or digested with endonucleases to obtain a desired range of DNA fragment lengths (e.g., 0.5 kilobases to 5 kilobases, especially 1 to 2 kilobases). The genomic DNA can also be chemically fragmented as described in Iverson et al., *Nucl. Acids Res.*, 15:7823, 1987; and Proudnikov et al., *Anal. Biochem.*, 259:34–41, 1998. Nucleic acid isolation from cells and cDNA synthesis can be performed by standard techniques well known in the art. In addition, commercial kits for carrying out these procedures are readily available.

Once the sample nucleic acid has been isolated and purified as needed, the nucleic acid is linked to a solid support. Examples of solid supports include beads, e.g., made of polystyrene or cross-linked agarose, and slides, e.g., of glass or plastic. Beads are particularly suitable because they maximize the surface area on which the nucleic acid is presented for subsequent BCT reactions. In addition, amino activated beads, such as EAH Sepharose (Pharmacia Biotech, Piscataway, N.J.), amino-functionalized magnetic beads of iron-oxide (Advanced Magnetics, Inc., Cambridge, Mass.), and amino-functionalized polystyrene microspheres (Polysciences, Inc., Warrington, Pa.) are readily available and facilitate the attachment and subsequent removal of nucleic acids.

Glass slides, on the other hand, are particularly suitable when the BCT-labeled nucleic acid is hybridized to another nucleic acid while still linked to the solid support. If any fluorescent labels are to be detected after hybridization, chromium-plated glass slides offer the advantages of low background fluorescence and a strong non-covalent bond between the sample nucleic acid and the solid support. Further details on the use of chromium-plated glass slides as a solid support for nucleic acids can be found in U.S. patent application Ser. No. 09/085,625.

For covalent attachment of the nucleic acid to the solid support, any number of chemical reactions well known in the art can be used. For example, BCT is used not only for labeling nucleic acids, but also to attach nucleic acids to solid supports (U.S. Pat. No. 5,082,935). In addition, 1-ethyl-3-(dimethylaminopropyl)carbodiimide (EDAC) can be used to link a terminal phosphate of a nucleic acid to an amino-functionalized solid support such as polystyrene (Zammatteo et al., *Anal. Biochem.*, 236:85–94, 1996 and references therein) via a carbodiimide condensation reaction.

Bisulfite-Catalyzed Transamination of Nucleic Acids

Bisulfite-catalyzed transamination of nucleic acids is a specific reaction which links a reactive group to the $N^4$ atom in cytidine. The detectable label is linked to the reactive group before, during, or after the BCT reaction, thereby labeling the nucleic acid. BCT chemistry is further described in Schulman et al., *Nucl. Acids Res.,* 9:1203–1216 (1981); Gilliam et al., *Anal. Biochem.,* 157:199–207 (1986); Hayatsu, *Prog. Nucl. Acid Res. Mol. Biol.,* 16:75–124 (1976); and Draper, *Nucl. Acids Res.,* 12:989–1002 (1984).

The starting reactive group employed in BCT can be an organic compound with at least two substituents. The first substituent is capable of reacting with cytidine nucleotides in a nucleic acid. Examples of the first substituent include alkyl amino (primary and secondary), hydrazido, semicarbazido, thiosemicarbazido, and acylhydrazido moieties.

The second substituent of the reactive group is capable of reacting with a detectable label molecule. The second substituent can be blocked or unblocked to guard against promiscuous reactivity during the linking of the cytidine to the reactive group via the first substituent. Whether blocked or unblocked, the second substituent should be substantially non-reactive with other molecules in the transamination reaction linking the reactive group to the cytidine. Examples of second substituents include amino, carboxyl, phosphate, sulfonate, sulfhydryl, hydroxyl, hydrazido, semicarbazido, and thiosemicarbazido. Carboxyl groups can be in either salt, acid, or ester form. When in salt form, the cation can be an alkali metal such as sodium or potassium.

In an organic reactive group, the first and second substituents can be on adjacent carbon atoms or spaced further apart. The reactive group can be a straight, branched, or cyclic hydrocarbon and includes an ether or thioether linkage.

Another example of a suitable reactive group is a diamine. As a diamine, the reactive group can include propylene, butylene, pentylene, hexylene, and nonylene groups, such as $CH_3NH(CH_2)_2NH_2$ and $CH_3NH(CH_2)_2NHCH_3$. Diamines incorporating hydroxylated hydrocarbons are also suitable reactive groups, including 1,3-diamino-2-hydroxypropane; 1,4-diamino-2,3-dihydroxylbutane; 1,5-diamino-2,3,4-trihydroxylpentane; 1,6-diamino-1,6-dihydroxy-D-mannitol; 1,6-diamino-2,3,4,5-tetrahydroxy hexane; trans-1, 2-diamino-3,4,5,6-tetrahydroxycyclohexane.

Other suitable reactive groups include certain amino acids, isopipecolinic acid, glucosaminic acid, and 6-aminohexanoic acid. The reactive group can have a molecular weight below 1000 daltons (e.g., below 500, 250, 100, or 50 daltons). Not all amino acids are appropriate, since some contain functionalities that could be damaged in the BCT reaction. For example, sulfur-containing amino acids such as cystine or cysteine may not be suitable. On the other hand, methionine can be suitable, since the sulfur is in the form of a sulfide. Of course, some amino acids, e.g., alanine, glycine, valine, and isovaline, contain side chains that do not permit further elaboration. Lysine or ornithine are particularly useful amino acids.

Peptides are particularly suitable reactive groups because peptide chains can contain a pre-attached dye molecule whose fluorescence is enhanced by the chemical environment provided by the linking peptide. These dye molecules can have molecular weights between 500 and 10,000 daltons. Solubility is a constraining factor since, for BCT to occur at a useful rate, relatively high concentrations of the reactive ligand are required (0.02 to 2 M, especially 0.2 to 2 M).

To increase efficiency of the chemistry, the BCT reaction can be performed in a chaotrope anion solvent such as trihaloacetate. It is known that nucleic acids forming secondary structure are less susceptible to BCT. Since chaotropes can help maintain the nucleic acid in a denatured or single-stranded structure, its inclusion in the BCT reaction mixture is a desirable option. Trifluoroacetic acid (TFA) has been found to be especially suitable for nucleic acid transamination reactions.

Linking Detectable Labels to Reactive Groups

The starting detectable label molecules employed in the practice of this invention contain at least one label moiety that is capable of reacting with the second substituent of the reactive group. The label moiety can be an amino, carboxyl, aldehyde radical, isothiocyanate, N-hydroxysuccinimide ester, sulfonyl halide, or carboxylic acid group. The specific label moiety desired depends on the nature of the second substituent of the reactive group, and, similarly, the choice of a second substituent is dependent on the label moiety to be used. To minimize interference with hybridization of the sample nucleic acid to a target, the label molecule should be less than 5000 daltons (e.g., less than 2500, 1000, or 500 daltons).

If the detectable label molecule is a fluorophore, the fluorophore can have an extinction coefficient of at least about 6,000 $M^{-1}cm^{-1}$ (e.g., at least 10,000 $M^{-1}cm^{-1}$) at an excitation wavelength, and a quantum yield of at least about 0.02. Examples of detectable label molecules include amino-functionalized fluorophores available from Molecular Probes, Inc., Eugene, Oreg., such as 7-amino-4-methylcoumarin-3-acetic acid, succinimidyl ester (AMCA); sulforhodamine 101 sulfonyl chloride (Texas Red™); S-(and 6-)caroxylrhodamine 101, succinimidyl ester; lissamine rhodamine B sulfonyl chloride; 5-(and 6-)carboxylfluorescein, succinimidyl ester; 7-diethylaminocoumarin-3-carboxylic acid, succinimidyl ester; tetramethylrhodamine-5-(and 6-)isothiocyanate; N-(4, 4-difluoro-5,7-dimethyl-4-bora-3a,4a-diaza-3-indacenepriopionic acid, succinimidyl ester; activated fluorescein derivative (FAP); eosin-5-isothiocyanate; erythrosin-5-isothiocyanate, and an O-acetylazide derivative of 1-hydroxy-3,6,8-pyrenetrisulfonoic acid (Cascade Blue™ acetylazide).

The reaction conditions for linking the reactive group to the detectable label are well known in the art (see, e.g., U.S. Pat. No. 5,506,250).

Uses

The methods of the invention can be performed by laboratory personnel of ordinary ability in the art of biochemistry or molecular biology. For example, the laboratory worker can use a kit of the invention, which includes a solid support (e.g., amino-activated Sepharose beads), a bisulfite solution, a reactive group (e.g., ethylenediamine), and a detectable label (e.g., an amino-activated fluorophore), to chemically label the nucleic acid with any of several fluorophores on, e.g., a 5.0 μg to 1.0 mg scale. Once the nucleic acid sample to be labeled is purified and/or isolated, the nucleic acid is linked to the beads and labeled as described above. Each step of the reaction is facilitated by the use of the beads, which allows quick washing steps using centrifugation.

Alternatively, the kit can include a 96-well microtiter plate made of polystyrene, each well of which can be amino-functionalized using standard techniques. Multiple nucleic acid samples can then be linked to the wells and labeled in parallel, while keeping each nucleic acid sample separate from the others.

In addition, rather than having a laboratory worker perform the reaction steps, automated or robotic devices can be used to process and label large numbers (hundreds to thousands) of nucleic acid samples in parallel and/or in series. Suitable devices and systems for automating the methods of the invention include the Biomek 2000 system (Beckman Instruments, Inc., Fullerton, Calif.) and the BioRobot 9600 system (Qiagen, N.V., Venlo, The Netherlands). Both the Biomek 2000 and BioRobot 9600 products utilize integrated computer control and monitoring as necessary for performing the methods of the invention.

The compositions and kits of the invention also include microchips, which can be used in the methods of the invention. The term microchip or "chip" is used herein to describe microarray devices used for DNA analysis. These microdevices consist of two-dimensional arrays of locus specific DNA sequences immobilized on a suitable glass or chromium coated glass surface. The arrays of surface-bound DNA fragments can be used to simultaneously analyze hundreds of genetic loci in a test specimen (usually green fluorescently labeled) by hybridization when this test DNA is co-hybridized to the chip surface with, e.g., a red fluorescent-labeled, reference DNA. Measurement of green/red fluorescence ratios then provides a measure of relative copy number at the particular loci represented by the surface array of dotted DNAs.

However in the MEMS (miniaturized electromechanical systems) field in general, the term microchip is used in a much broader sense to describe any of a number of miniaturized devices capable of carrying out a variety of mechanical or chemical sensing operations such as motion sensing (air bag deployment sensors), ink-jet print heads or biochemical sensors (portable blood analyzers). These MEMS devices are typically micromachined in silicon wafers by high-definition surface etching techniques routinely practiced by those in the field. MEMS devices constructed from glass or plastic can also be produced. In many chemical sensing applications fluids are moved in silicon-etched channels by miniature diaphragm pumps or in glass-channels by electro-osmotic flow (EOF) produced by a applying a voltage across the channel. Devices in which fluids flow along microchannels are termed microfluidics devices. A timely review of the current state of microfluidics system development can be found in Chemical & Engineering News, Feb. 22, 1999, pp27–36. (American Chemical Society, Washington D.C., USA).

Automated direct labeling can also be practiced on a microfluidics device or "pillar chip" manufactured by Cepheid Inc., Sunnyvale, Calif. (www.cepheid.com) and described in Petersen et al., *IVD Technol.* 4:43–49, 1998. These pillar chips (approx. 5×5 mm$^2$) are made of thousands of silicon fingers (200 μm high and 34 μm on center) protruding into a tiny chamber (3.5 mm$^2$ with a total internal surface area of 36 mm$^2$) etched into a silicon wafer. The chamber is sealed by a glass cover plate bonded to the wafer. Fluids are introduced into the chip by inlet and outlet ports machined into the chip at diagonal opposites.

As first produced, the chip is pure silicon which is not conducive to attachment of biological ligands. However, if the surface is oxidized to produce a thin layer of silicon dioxide, then a number of different surface modification chemistries can be used. For example, by using silane activating agents, the silicon oxide surface can be functionalized with, for example, amino, sulfhydryl, hydroxyl or epoxide reactive groups that subsequently can be used to attach biochemical ligands to the surface. For example, reaction of the silicon dioxide chip surface with 3-aminopropyltrimethoxysilane produces a surface modified with amino groups to which double-stranded or single-stranded DNA oligonucleotides containing a terminal phosphomonoester group can be covalently attached by the EDAC carbodiimide coupling means used to attach these nucleic acids to polymeric beads as described herein. Also see Joos et al., *Anal. Biochem.* 247:96–101, 1997 which describes carbodiimide-activated attachment of carboxylated oligonucleotides to aminopropylsilane-modified glass solid phases.

The amino functionalized chip surface can also react with nucleic acids by means of the BCT reaction described in U.S. Pat. No. 5,091,519. For in situ synthesis of oligos on an epoxide-modified glass microscope slide surface, see Maskos et al., *Nuc. Acids Res.* 20:1679–1684, 1992, and references therein. If the epoxide functionalized glass surface is converted to a hydroxyl surface as taught by Maskos et al., supra, then attachment of nucleic acids by cyanogen bromide activation is possible. For attachment of oligos to a sulfhydryl modified glass slide surface, see, e.g., Rogers et al., *Anal. Biochem.* 266:23–30, 1999.

Reversible attachment of DNA can be achieved with the EDAC/phosphoramidate procedure described above. A sulfhydryl solid phase and disulfide linkage between the DNA and support is cleavable with reducing agents but a disulfide bond is not stable to the BCT conditions.

With a total internal surface area of approximately 0.3 cm$^2$, and a theoretical maximum binding efficiency of $10^{14}$ molecules/cm$^2$ (approx. $5 \times 10^{-11}$ moles/chip), the chip is capable of binding approximately 8 μg of a 500 bp double-stranded genomic DNA fragment. Even if the actual loading capacity is 1–5% of theoretical, then the chip should be capable of labeling enough genomic DNA for analysis on a DNA microarray.

Another approach that can be used with the pillar chip (or with beads) is to enzymatically label the DNA, for example, by nick translation with fluorescent nucleotides while the DNA is still attached to the solid phase. The DNA can be released from the solid phase, mixed with reference DNA, and swept onto a microarray. The future may hold the microarray as one component of an integrated microfluidics analysis system capable of DNA isolation, labeling, hybridization, and analysis.

EXAMPLES

The invention will be further described in the following examples, which do not limit the scope of the invention described in the claims.

Example 1

Bisulfite-Mediated Fluorescent Labeling of a Nucleic Acid on a Solid Support

Fifty microliters of commercial aminated diaminodipropylamine (DADPA) beads (Pierce Catalog No. 53147) were mixed with 50 μg of sonicated, heat denatured human placental genomic DNA in the presence of 0.2 M 1-ethyl-3-(dimethylaminopropyl)carbodiimide (EDAC) and 0.1 M 2-(N-morpholino)ethanesulfonic acid (MES, pH 6.0). The mixture was incubated for one hour at 50° C. In a separate experiment, room-temperature incubation overnight was also sufficient to link the DNA to the beads.

This solid phase linking procedure was found to strongly bind about 35 μg of the 50 μg starting DNA. The linkage was stable to an incubation in 0.2 M MOPS (pH 7.4) or 50 mM NaCl at 65° C. for up to 310 minutes. About 10 μg of the 50

μg starting DNA was weakly bound to the beads and could be removed by incubating the DNA/bead mixture in 62.5 mM sodium borate and 1.25 M NaCl (pH 8.5) at 65° C. for six or more minutes.

The beads were then washed five times, one minute each wash, with double distilled water (ddH$_2$O). Washing was performed by centrifugation, removing the supernatant, and then resuspending in water. The DNA was denatured at 95° C. for five minutes, followed by snap-cooling by immersing in an ice bath. It was found that about 33 μg of the 50 μg starting DNA was still bound on the beads after denaturation and cooling.

A transamination buffer was prepared by adding 1.53 ml of trifluoroacetic acid (TFA) to 2.5 ml of deionized water. The buffer was allowed to cool for 10 minutes. 0.87 ml of ethylenediamine (free base; Sigma Catalog. No. E 4379) was then slowly added to the buffer on ice. After dissolution of the ethylenediamine, the buffer was warmed to room temperature. 0.475 g sodium metabisulfite (Aldrich Catalog No. 25,555–6) was added to the buffer, and the buffer was warmed to 45° C. to dissolve the bisulfite. The pH of the buffer was adjusted to 7.0 by addition of TFA, and the volume of the buffer was adjusted to 5 ml. 50 μl of a 100 mg/ml solution of hydroquinone was then added to the buffer.

To transaminate the immobilized DNA, 125 μl of bisulfite transamination buffer was added to the DNA/bead mixture, and the mixture incubated for 20 minutes at 65° C. to attach the ethylenediamine to the cytosines in the DNA. In a separate experiment, transaminating the DNA at room temperature overnight was also found to be acceptable. The beads were again washed 5× with ddH$_2$O to remove excess buffer.

The beads were then suspended in 550 μl of carboxyXrhodamine NHS ester labeling buffer (2–5 mM fluorophore in 62.5 mM sodium borate, 1 M NaCl [pH 8.5], and 15% [v/v] DMF). The beads were incubated in the labeling buffer for one hour at 50° C., then washed 5× with ddH$_2$O to remove the labeling buffer. In a separate experiment, labeling was achieved at room temperature for 16 hours.

To release the labeled DNA, the beads were incubated in 0.1 ml of 50 mM NaOH at 65° C. for one hour. (Though time consuming, the DNA could also be released from the beads by incubating in formamide at 75° C. for 72 hours. The formamide denaturing solution was prepared by mixing together 49 ml of formamide, 7 ml of 20×SSC, 14 ml water, resulting in a 70% formamide solution at a pH of 7.5.) About 15 μg of labeled DNA was recovered by this first incubation. About another 10 μg of DNA were recovered by an additional one hour treatment in 50 mM NaOH at 65° C. In general, efficiency of DNA release can be optimized by changing time, temperature, pH, or adding a catalyst. The labeled DNA solution was neutralized with 0.1 volume of 3 M sodium acetate to bring the pH to 6.0. The DNA was then isolated by ethanol precipitation.

The procedure above was repeated to label human placental genomic DNA with 6-(fluorescein-5-(and-6) carboxamido)hexanoic acid NHS ester and 5,6-carboxytetramethylrhodamine NHS ester.

Example 2

Use of Fluorescently Labeled Nucleic Acid for Visualizing Metaphase Chromosomes

The 5,6-carboxyXrhodmaine NHS ester, 6-(fluorescein-5-(and-6)-carboxamido)hexanoic acid NHS ester, and 5,6-carboxytetramethylrhodamine NHS ester labeled DNA as prepared in Example 1 above were each separately hybridized to human primary lymphocyte metaphase chromosomes in situ as described in U.S. Pat. No. 5,776,688. The labels were specific for chromosome structures, and signal intensities were moderate to good for all three labels.

Example 3

Use of Fluorescently Labeled Nucleic Acid on AmpliOnc® Biochip 6-(fluorescein-5-(and-6)carboxamido)hexanoic acid NHS ester-labeled test DNA from human colon cancer cells (colo 320) and 5,6-carboxyXrhodamine NHS ester-labeled normal human reference DNA were prepared as follows.

Sonicated colo 320 DNA (50 μg in 50 μl; average fragment size 300 to 3000 bp) was heat denatured at 95° C. for 5 minutes and snap-cooled on ice. 50 μl of DADPA bead suspension (Pierce) was repeatedly washed in water and suspended in water so that the final volume of beads plus supernatant was 25 μl. To the bead suspension was added the DNA solution, followed by the addition of 25 μl of 0.5 M MES buffer and 25 μl of 0.5 M EDAC. The mixture was heated at 50° C. for one hour. The beads were isolated by filtration and washed 5 times with 250 μl of water. Finally the beads were suspended in 100 μl water. A 10 μl aliquot of this bead suspension released 3.1 μg of DNA when treated with 50 mM NaOH at 65° C. for one hour.

Ten microliters of bead suspension was removed (nominally equivalent to 5 μg of DNA assuming all input DNA had become bound) and suspended in 50 μl of water. The mixture was heated at 95° C. for 5 minutes and snap-cooled on ice. The beads were isolated by centrifugation, the supernatant removed, and freshly prepared TFA amination mixture (125 μl) that had been prewarmed to 65° C. was added. The mixture was heated at 65° C. for 10 minutes. The amination reaction was immediately cooled on ice and the beads repeatedly washed in water.

The beads were suspended in 110 μl of labeling buffer (0.1 M sodium borate; 1 M sodium citrate, pH 8.2). Then 22 μl of 6-(fluorescein-5-(and-6)-carboxamido)hexanoic acid NHS ester (FCHA-NHS, 20 mM in DMF) was added. The mixture was heated at 50° C. for one hour. The beads were isolated by centrifugation and washed repeatedly with water.

The beads were suspended in 100 μl of 50 mM NaOH and heated at 65° C. for one hour. The beads were removed by centrifugation through a centrifuge filter, and the filtrate containing the finished labeled probe was collected.

To the filtrate was added 0.1 volume of sodium acetate and 2.0 volumes of ethanol. The mixture was chilled at −20° C. for 15 minutes, and the DNA pelleted by centrifugation. The pellet was washed with 70% aqueous ethanol and further purified by dissolution in 60 μl water, followed by passage through a Biospin 30 column (BioRad, Hercules, Calif.). The final volume of probe solution was 65 μl.

Fifteen microliters of the probe solution were combined with 100 μg of Cot 1 DNA (blocking DNA; see below) and 200 ng of 5,6-carboxyXrhodamine-labeled male reference DNA. The DNA mixture was then precipitated with ethanol as described above. The Cot-blocked colo 320 DNA was hybridized on microscope slides coated with human lymphocytes using standard protocols (see Example 2). The amplified c-myc locus on chromosome 8 that was present in the colo 320 cell line, appeared as two green fluorescing dots in metaphase nuclei with good signal intensity and background.

Fifteen microliters of FCHA labeled colo 320 probe and 5 µl (500 ng) of 5,6-carboxyXrhodamine-labeled male reference DNA were evaporated to dryness in a SpeedVac concentrator. To 5.4 µl of water was added 5.4 µl (100 µg) of Cot 1 DNA and 16.2 µl of hybridization buffer (50% formamide, 2×SSC, 10% dextran sulfate). The probe DNA mixture was heat denatured at 80° C. for 10 minutes, pre-hybridized at 37° C. for 2 hours, applied to the AmpliOnc™ microarray, and hybridized at 37° C. overnight. The chips were removed from the 37° C. incubator and washed. The chips were washed 3 times for 2 minutes at room temperature in 1×SSC, followed by washing 3 times for 10 minutes at 40° C. in 50% formamide/2×SSC, and finally washing 3 times for 2 minutes at room temperature in 1×SSC. The microarray was allowed to air dry for several minutes. Gel mount containing DAPI counterstain was added and the green/red fluorescence ratios quantitated on an in-house fluorescence imaging instrument (see below).

The cancer cell DNA is known to have an amplified c-myc gene. The labeled DNAs were used to hybridize to an AmpliOnc™ (Vysis, Inc.) DNA biochip.

The AmpliOnc™ chip contains a microarray of nucleic acids representing genes known to be involved in human cancers. Negative control dots, e.g., containing lambda phage DNA, are also included. Each cancer gene is represented by five identical spots on the microarray. In use, the AmpliOnc™ chip is hybridized with a normal reference DNA sample labeled with a fluorophore of one color, and a test DNA sample labeled with a fluorophore of another color. To detect an amplified cancer gene, all dots representing that gene will be disproportionately colored by the fluorophore associated with the test DNA. Dots representing unamplified genes should have about equal amounts of both fluorophores.

An AmpliOnc™ chip was hybridized with 25 µl of hybridization buffer at 37° C. for 16 hours. The hybridization buffer was 2×SSC supplemented with 50% (v/v) formamide, 4 µg/µl Cot 1 DNA, 500 ng of 6-(fluorescein-5-(and-6)-carboxamido)hexanoic acid NHS ester-labeled Colo 320 DNA, and 500 ng of SpectrumRed human reference DNA. The Cot 1 DNA is a fraction of human genomic DNA rich in repeat elements and is used to suppress or block hybridization of repeat elements that are always present in the labeled DNA probe isolated from a human test specimen. Signals from the repeat elements would confuse and obscure the signal from unique sequence DNA. The chip was then washed and imaged using standard protocols.

Quantitative determinations of signals emanating from the chip were carried out with a large field fluorescent imaging system developed at Vysis, Inc. (Downers Grove, Ill.). The imaging system consisted of a 450 W Xenon arc lamp (SLM Instruments Inc., Champaign Urbana, Ill.), a charge coupled device detector (CH200, Photometrics, Tucson, Ark.), and a filter set (Chroma Technology, Brattleboro, Vt.) for three commonly used fluorescent dyes—DAPI for blue, fluorescein isothiocyanate ("FITC") for green, and Texas red ("TRED") for red. The imaging system was controlled by a Power Macintosh 7100/80 with an imaging acquisition/analysis software (IpLab, Signal Analytics, Corp., Vienna, Va.).

The fluorescence background of the hybridized chip was low and comparable to nick translation-labeled DNA. The green and red fluorescence for each dot were quantified, and the data summarized in Table 1.

TABLE 1

| Targets | Blue | Green | Red | G/R |
|---|---|---|---|---|
| 1 TTL Hum-DNA | 261 ± 25 | 148 ± 20 | 338 ± 45 | 0.54 ± 0.01 |
| 2 Lambda | 547 ± 164 | 6 ± 2 | 7 ± 4 | 1.04 ± 0.13 |
| 3 PDGFB | 530 ± 21 | 36 ± 5 | 31 ± 4 | 1.41 ± 0.05 |
| 4 EGFR | 550 ± 31 | 13 ± 3 | 19 ± 3 | 0.81 ± 0.09 |
| 5 PDGFRA | 873 ± 130 | 37 ± 3 | 48 ± 6 | 0.95 ± 0.04 |
| 6 MYB | 745 ± 71 | 83 ± 8 | 89 ± 7 | 1.16 ± 0.03 |
| 7 WNT1 | 705 ± 21 | 53 ± 14 | 66 ± 15 | 0.98 ± 0.09 |
| 8 HRAS1 | 773 ± 41 | 62 ± 3 | 71 ± 3 | 1.09 ± 0.03 |
| 9 MET | 893 ± 101 | 40 ± 7 | 36 ± 5 | 1.38 ± 0.04 |
| 10 BEK | 1305 ± 40 | 48 ± 10 | 61 ± 13 | 0.97 ± 0.03 |
| 11 HER2 | 1236 ± 37 | 173 ± 36 | 151 ± 30 | 1.41 ± 0.03 |
| 12 BCL1/CYC-D | 688 ± 92 | 40 ± 5 | 53 ± 4 | 0.91 ± 0.06 |
| 13 YES1 | 1187 ± 93 | 54 ± 10 | 77 ± 14 | 0.88 ± 0.02 |
| 14 RAF1 | 957 ± 102 | 54 ± 4 | 62 ± 5 | 1.08 ± 0.03 |
| 15 GL1 | 836 ± 34 | 68 ± 13 | 53 ± 10 | 1.59 ± 0.05 |
| 16 MDM2 | 1398 ± 226 | 44 ± 5 | 67 ± 7 | 0.82 ± 0.03 |
| 17 C-MYC | 795 ± 100 | 755 ± 79 | 39 ± 4 | 23.93 ± 0.94 |
| 18 AMP.20Q | 1345 ± 106 | 68 ± 12 | 63 ± 11 | 1.33 ± 0.07 |
| 19 REL | 1339 ± 124 | 87 ± 14 | 84 ± 14 | 1.28 ± 0.06 |
| 20 MYCL1 | 1551 ± 101 | 66 ± 5 | 66 ± 6 | 1.24 ± 0.11 |
| 21 FGR | 863 ± 190 | 54 ± 17 | 59 ± 17 | 1.13 ± 0.05 |
| 22 FES | 981 ± 196 | 74 ± 10 | 64 ± 6 | 1.42 ± 0.11 |
| 23 ABL | 707 ± 85 | 62 ± 12 | 65 ± 14 | 1.19 ± 0.04 |
| 24 INT2 | 1335 ± 73 | 136 ± 26 | 157 ± 31 | 1.09 ± 0.07 |
| 25 PIK3CA | 1452 ± 351 | 36 ± 8 | 37 ± 7 | 1.19 ± 0.07 |
| 26 N-MYC | 1277 ± 55 | 65 ± 9 | 69 ± 7 | 1.16 ± 0.07 |
| 27 AKT2 | 1167 ± 95 | 105 ± 9 | 90 ± 10 | 1.46 ± 0.06 |
| 28 FLG | 1660 ± 217 | 141 ± 17 | 135 ± 16 | 1.29 ± 0.05 |
| 29 JUNB | 1652 ± 69 | 202 ± 7 | 148 ± 6 | 1.68 ± 0.03 |
| 30 AKT1 | 810 ± 74 | 78 ± 10 | 89 ± 8 | 1.09 ± 0.05 |
| 31 KRAS2 | 1171 ± 78 | 49 ± 3 | 58 ± 5 | 1.05 ± 0.03 |
| 32 CDK4/SAS | 1399 ± 111 | 148 ± 23 | 152 ± 23 | 1.20 ± 0.04 |
| 33 ANDRO. REC. | 1278 ± 133 | 136 ± 16 | 88 ± 8 | 1.91 ± 0.04 |
| 34 CMIX 3-12 | 1334 ± 45 | 185 ± 18 | 286 ± 34 | 0.80 ± 0.02 |
| 35 CMIX 13-22 | 1813 ± 82 | 926 ± 115 | 321 ± 35 | 3.55 ± 0.05 |
| 36 CMIX 23-32 | 1510 ± 130 | 274 ± 20 | 338 ± 20 | 1.00 ± 0.02 |

Each value in Table 1 is reported with its standard deviation. The blue fluorescence is from DAPI—a general DNA counterstain required for confirming the presence of DNA at the spot location. The expected amplification of the c-myc oncogene in Colo 320 DNA was indicated by the high green fluorescence (755 counts) for Colo 320 DNA, as compared to the relatively low red fluorescence (39 counts) for normal human DNA, yielding a 24-fold amplification (target 17 in Table 1). In addition, the low level of labeled DNA bound to the lambda phage dots indicated little non-specific binding.

Other Embodiments

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

What is claimed is:

1. A method for linking a detectable label to a nucleic acid, the method comprising providing a nucleic acid bound to a solid support, the nucleic acid comprising a cytidine base;

transaminating the cytidine base with a reactive group to form a covalent linkage between the cytidine base and the reactive group; and linking a detectable label to the reactive group.

2. The method of claim 1, wherein the solid support is a bead.

3. The method of claim 1, wherein the solid support is a chromium-plated glass slide.

4. The method of claim 1, wherein the transaminating step is catalyzed by a bisulfite.

5. The method of claim 1, wherein the reactive group comprises the formula:

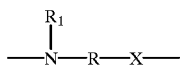

wherein

R is an alkylene radical containing 2 to 14 carbon atoms inclusive;

X is a divalent radical selected from the group consisting of

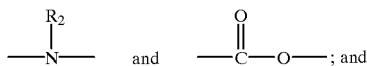

$R_1$ and $R_2$ are each independently selected from the group consisting of hydrogen and a lower alkyl.

6. The method of claim 5, wherein the reactive group is ethylenediamine.

7. The method of claim 1, wherein the reactive group is dissolved in a solvent comprising a trihaloacetate chaotrope anion.

8. The method of claim 7, wherein the trihaloacetate chaotrope anion is trifluoroacetate.

9. The method of claim 1, wherein the detectable label is a fluorescent molecule.

10. The method of claim 1, wherein the nucleic acid is about 1 to 2 kilobases in length.

11. The method of claim 1, further comprising releasing the nucleic acid from the solid support.

12. The method of claim 1, wherein the nucleic acid is covalently bound to the solid support.

13. The method of claim 12, wherein the nucleic acid is bound to the solid support by reacting a terminal phosphate of the nucleic acid and an amino activated solid support with 1-ethyl-3-(dimethylaminopropyl)carbodiimide.

14. A composition comprising a solid support;

a nucleic acid bound to the solid support, the nucleic acid comprising a cytidine base;

a reactive group covalently linked to the cytidine base; and a detectable label linked to the reactive group.

15. The composition of claim 14, wherein the solid support is a bead.

16. The composition of claim 14, wherein the solid support is a chromium-plated glass slide.

17. The composition of claim 14, wherein the reactive group comprises the formula:

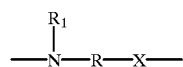

wherein

R is an alkylene radical containing 2 to 14 carbon atoms inclusive;

X is a divalent radical selected from the group consisting of

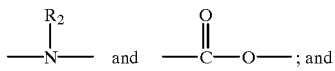

$R_1$ and $R_2$ are each independently selected from the group consisting of hydrogen and a lower alkyl.

18. The composition of claim 17, wherein the reactive group is ethylenediamine.

19. The composition of claim 14, wherein the detectable label is a fluorescent molecule.

20. The composition of claim 14, wherein the nucleic acid is about 1 to 2 kilobases in length.

21. The composition of claim 14, wherein the nucleic acid is covalently bound to the solid support.

22. The composition of claim 21, wherein the nucleic acid is bound to the solid support by reacting a terminal phosphate of the nucleic acid and an amino activated solid support with 1-ethyl-3-(dimethylaminopropyl) carbodiimide.

23. A method for linking a detectable label to a plurality of nucleic acids, each of the plurality having a unique sequence, the method comprising providing the plurality of nucleic acids bound to a solid support, each of the plurality comprising a cytidine base;

transaminating each cytidine base with reactive groups to form a covalent linkage between each cytidine base and a reactive group; and linking a detectable label to the reactive groups.

24. The method of claim 1, wherein the reactive group comprises $H_2N(CH_2CH_2X)_nCH_2CH_2NH_2$, wherein n=1–4, X is O, SO, $SO_2$, Si, or $NR_3$, wherein $R_3$ is a lower alkyl.

25. The composition of claim 14, wherein the reactive group comprises $H_2N(CH_2CH_2X)_nCH_2CH_2NH_2$, wherein n=1–4, X is O, SO, $SO_2$, Si, or $NR_3$, wherein $R_3$ is a lower alkyl.

26. A kit comprising a solid support;

a bisulfite;

a reactive group; and a detectable label.

27. The kit of claim 26, wherein the solid support is a bead.

* * * * *